US005919742A

United States Patent [19]

Tsuzuki et al.

[11] Patent Number: 5,919,742

[45] Date of Patent: Jul. 6, 1999

[54] CONTACT LENS CLEANING MATERIAL FORMED OF A POLYMER

[75] Inventors: Akira Tsuzuki, Nagoya; Sadayasu Tanikawa, Kasugai, both of Japan

[73] Assignee: Menicon Co., Ltd., Japan

[21] Appl. No.: 08/901,773

[22] Filed: Jul. 28, 1997

[30] Foreign Application Priority Data

| | | | |
|---|---|---|---|
| Jul. 29, 1996 | [JP] | Japan | 8-198662 |
| Jul. 14, 1997 | [JP] | Japan | 9-188368 |

[51] Int. Cl.$^{6}$ .............................. C11D 3/37; C11D 17/00; A61L 2/18; G02C 13/00

[52] U.S. Cl. .......................... 510/112; 510/383; 510/384; 510/403; 510/434; 510/445; 510/455; 510/475; 510/476

[58] Field of Search ............................ 510/112–115, 475, 510/476, 403, 434, 445, 455, 383, 384–386

[56] References Cited

U.S. PATENT DOCUMENTS

| | | | |
|---|---|---|---|
| 4,655,957 | 4/1987 | Chromecek et al. | 510/113 |
| 4,783,340 | 11/1988 | McDonnell et al. | 428/28 |
| 5,302,312 | 4/1994 | Kawai et al. | 510/113 |
| 5,358,688 | 10/1994 | Robertson | 422/28 |
| 5,447,560 | 9/1995 | Vogel | 523/201 |
| 5,461,433 | 10/1995 | Nakabayashi et al. | 510/112 |
| 5,538,663 | 7/1996 | Kihara et al. | 510/395 |
| 5,721,313 | 2/1998 | Yeung et al. | 524/814 |

*Primary Examiner*—Ardith Hertzog
*Attorney, Agent, or Firm*—Parkhurst & Wendel, L.L.P

[57] ABSTRACT

A cleaning material for a contact lens formed of a polymer which is obtained by polymerizing a polymeric composition including at least a nonionic surface active agent having a polymerizable unsaturated double bond, and a cross-linking agent having a plurality of polymerizable unsaturated double bonds.

13 Claims, No Drawings

CONTACT LENS CLEANING MATERIAL FORMED OF A POLYMER

BACKGROUND OF THE INVENTION

1. Field of the Invention

The present invention relates to a cleaning material for a contact lens. More particularly, the present invention is concerned with a contact lens cleaning material is capable of effectively cleaning the contact lens in a simplified manner with a sufficiently high degree of detergency and which is easy to carry around, assuring excellent portability.

2. Discussion of the Related Art

For removing stains adhering to a contact lens while the contact lens is worn on an eye of a user, there are proposed various kinds of cleaning agents and cleaning devices. Any one of those cleaning agents and cleaning devices or any combination thereof is conventionally used for cleaning the contact lens.

Generally, when the cleaning agent is used to clean the contact lens, the contact lens is cleaned by rubbing, using the cleaning agent (liquid agent), so as to remove the stains adhering to the contact lens, and then rinsed by a rinsing liquid (which functions also as a storing liquid). This procedure for cleaning the contact lens requires at least two kinds of liquid agents, i.e., the cleaning agent and rinsing liquid. In general, liquid agents are bulky, and therefore low portability.

Recently, a so-called "all-in-one type" liquid agent for the contact lens is commercially available. This "all-in-one type" liquid agent has various functions such as a cleaning agent, storing agent and disinfecting agent, for instance. When such an all-in-one type liquid agent is used for cleaning the contact lens, it is not necessary to carry around two or more bottles of the cleaning agent, storing agent and disinfecting agent, respectively. However, in general, the detergency of the all-in-one type liquid agent tends to be low because of its diverse functions. Further, it undesirably takes a relatively long period of time to effect a cleaning treatment on the contact lens when the all-in-one type liquid agent is used to clean the contact lens.

When the cleaning device is used to clean the contact lens, there are some problems as indicated below. That is, the cleaning device is bulky in general, and therefore has low portability. Further, the cleaning device usually requires an electric power source for driving same. Thus, the use of the cleaning device to clean the contact lens usually requires a suitable electric power source.

As described above, the contact lens is cleaned conventionally by using the cleaning agent or cleaning device. Alternatively, the cleaning agent and the cleaning device are used in combination to clean the contact lens. However, in any case, there are some problems in view of the detergency and portability. Thus, it has been desired to develop a novel cleaning material for a contact lens that is capable of cleaning the contact lens in a simplified manner while exhibiting a considerably high degree of detergency and excellent portability.

SUMMARY OF THE PRESENT INVENTION

It is therefore an object of the present invention to provide a cleaning material for a contact lens having a suitable shape, which cleaning material is easy to carry around and is capable of cleaning the contact lens in a simplified manner while exhibiting a sufficiently high degree of detergency.

The above-indicated object of the invention may be attained according to a principle of the present invention which provides a cleaning material for a contact lens formed of a polymer which is obtained by polymerizing a polymeric composition including at least a nonionic surface active agent having a polymerizable unsaturated double bond, and a cross-linking agent having a plurality of polymerizable unsaturated double bonds.

The contact lens cleaning material according to the present invention is capable of effectively exhibiting an excellent cleaning effect since the cleaning material contains a unit of the nonionic surface active agent as one constituent of the polymer that gives the cleaning material. Further, since the present contact lens cleaning material is provided in the form of a gel which contains an aqueous component, it permits easy cleaning of the contact lens. In addition, the contact lens cleaning material of the present invention assures excellent portability, unlike the conventional bulky liquid-type cleaning agent and cleaning device which requires the electric power source.

In a first preferred form of the present invention, the nonionic surface active agent includes a polyoxyethylene chain in each molecule thereof.

In a second preferred form of the present invention, the nonionic surface active agent is included in the polymeric composition in an amount of not smaller than 5% by weight, so as to permit the contact lens cleaning material to exhibit a sufficient degree of cleaning effect.

In a third preferred form of the present invention, the cross-linking agent is included in the polymeric composition in an amount of 0.01–5% by weight.

In a fourth preferred form of the present invention, the polymeric composition further includes a disinfectant or germicide having a polymerizable unsaturated double bond. The contact lens cleaning material exhibits an excellent sterilizing effect in the presence of the disinfectant which is included in the cleaning material by polymerization of the polymerizable unsaturated double bond. Further, such a disinfectant is polymerized together with the nonionic surface active agent and the cross-linking agent as described above, so that it is chemically bonded to the constituents of the obtained cleaning material. Thus, the disinfectant is not eluted from the cleaning material. Accordingly, the present contact lens cleaning material is completely free from the problems that would be caused when the disinfectant is simply contained in the cleaning material. That is, the disinfectant eluted from the cleaning material may be bonded to the lens surface, or the disinfectant may permeate into the contact lens so that the disinfectant is stored in the contact lens, thereby giving an adverse influence on the eye of the user.

In one advantageous arrangement of the above fourth preferred form of the present invention, the disinfectant is a quaternary ammonium salt having a polymerizable unsaturated double bond.

In another advantageous arrangement of the above fourth preferred form of the present invention, the disinfectant is included in the polymeric composition in an amount of 0.01–10% by weight, so that the contact lens cleaning material can exhibit an excellent sterilizing effect.

In a fifth preferred form of the present invention, the polymeric composition further contains a hydrophilic monomer having a polymerizable unsaturated double bond, so that the obtained contact lens cleaning material has a suitable strength.

In a sixth preferred form of the present invention, the polymeric composition is dissolved in a solvent and polymerized, so as to increase compatibility and a degree of polymerization of the polymeric composition.

In a seventh preferred form of the present invention, the contact lens cleaning material has a content of an aqueous component in a range of 10–90%. The contact lens cleaning material containing a predetermined amount of the aqueous component takes a form of a gel. The thus prepared contact lens cleaning material has a suitable flexibility so as to permit easy cleaning of the contact lens. Further, the stains removed from the contact lens by the nonionic surface active agent are effectively absorbed by the aqueous component contained in the cleaning material. Thus, the present contact lens cleaning material permits effective cleaning of the contact lens and effective removal of the stains from the contact lens. Since the contact lens cleaning material contains the aqueous component, it does not give any damage or scratches to the contact lens while the contact lens is cleaned by the cleaning material.

In an eighth preferred form of the present invention, the contact lens cleaning material further includes a filler.

DETAILED DESCRIPTION OF THE PREFERRED EMBODIMENT

The cleaning material for the contact lens according to the present invention is formed of a polymer obtained by polymerizing a predetermined polymeric composition. The contact lens cleaning material of the present invention may easily take a form of a gel when it is impregnated with a suitable aqueous component. The polymeric composition which gives the polymer contains, as essential constituents, a nonionic surface active agent having a polymerizable (ethylenically) unsaturated double bond (hereinafter referred to as "polymeric nonionic surface active agent"), and a cross-linking agent having a plurality of polymerizable (ethylenically) unsaturated double bonds (hereinafter referred to as "cross-linking agent").

The polymeric nonionic surface active agent as one of the essential constituents of the polymeric composition is a nonionic surface active agent having a polymerizable unsaturated double bond such as (metha)acryloyl group, vinyl group, allyl group, or vinylphenyl group. Any kind of the nonionic surface active agent may be used provided that it is polymeric. In the specification, the term " . . . (metha) acryloyl . . . " is generic to the following two compounds: " . . . acryloyl . . . " and " . . . methacryloyl . . . ". This applies to the other terms such as " . . . (metha)acrylic acid . . . ", " . . . (metha)acrylate" and " . . . (metha)acrylamide".

The polymeric nonionic surface active agent is easily obtained by reacting a nonionic surface active agent having a hydroxyl group with an acid chloride having a polymerizable unsaturated double bond, for instance. Described more specifically, the polymeric nonionic surface active agent is formed by a dehydrochlorination reaction in which the nonionic surface active agent having the hydroxyl group is reacted with the acid chloride compound having the polymerizable unsaturated double bond by using a basic compound for dehydrochlorination, in a suitable solvent which does not inhibit the reaction. One example of the acid chloride is (metha)acrylic acid chloride and one example of the basic compound for the dehydrochlorination is triethylamine. As the solvent which does not inhibit the dehydrochlorination, tetrahydrofuran or dichloromethane is used, for instance.

The polymeric nonionic surface active agent is alternatively obtained by reacting the nonionic surface active agent having a hydroxyl group which is dissolved in a suitable solvent with metallic sodium, so as to provide a sodium alkoxide compound. The obtained sodium alkoxide compound is reacted with a halogenated compound having a polymerizable unsaturated double bond, so that the desired polymeric nonionic surface active agent is formed. As the solvent used in the reaction, it is preferable to select a solvent that does not contain a hydroxyl group and a nitrogen atom and that does not react with the metallic sodium and halogenated compound so as not to inhibit the intended reaction. One example of such a solvent is tetrahydrofuran. As the halogenated compound having the polymerizable double bond, p-chlormethylstyrene or allylchloride is used, for instance.

Examples of the nonionic surface active agent having the hydroxyl group used for forming the polymeric non-ionic surface active agent are the following: polyoxyethyleneglycerine fatty acid esters such as POE(5) glyceryl monostearate, POE(15) glyceryl monostearate, POE(5) glyceryl monooleate and POE(15) monooleate glyceryl; polyglycerine fatty acid esters such as diglyceryl monostearate, diglyceryl monooleate, diglyceryl dioleate, diglyceryl monoisostearate, tetraglyceryl monostearate, tetraglyceryl monooleate, tetraglyceryl tristearate, tetraglyceryl pentastearate, tetraglyceryl pentaoleate, hexaglyceryl monolaurate, hexaglyceryl monomyristate, hexaglyceryl monostearate, hexaglyceryl monooleate, hexaglyceryl trisstearate, hexaglyceryl pentastearate, hexaglyceryl pentaoleate, hexaglyceryl polyricinoleate, decaglyceryl monolaurate, decaglyceryl monomyristate, decaglyceryl monostearate, decaglyceryl monooleate, decaglyceryl monolinoleate, decaglyceryl monoisostearate, decaglyceryl distearate, decaglyceryl diisostearate, decaglyceryl tristearate, decaglyceryl trioleate, decaglyceryl pentastearate, decaglyceryl pentaoleate, decaglyceryl pentaisostearate, decaglyceryl heptastearate, decaglyceryl heptaoleate, decaglyceryl decastearate, decaglyceryl decaoleate, and decaglyceryl decaisostearate; sorbitan fatty acid esters such as sorbitan monolaurate, sorbitan monopalmitate, sorbitan monostearate, sorbitan sesquistearate, sorbitan tristearate, sorbitan monooleate, sorbitan sesquioleate, sorbitan trioleate, sorbitan monoisostearate, and sorbitan sesquiisostearate; polyoxyethylene sorbitan fatty acid esters such as POE(20) sorbitan monococonut oil fatty acid ester, POE(20) sorbitan monopalmitate, POE(20) sorbitan monostearate, POE(20) tristearate, POE(6) sorbitan monostearate, POE(20) sorbitan monooleate, POE(20) sorbitan trioleate, POE(6) sorbitan monooleate, and POE(20) sorbitan monoisostearate: polyoxyethylene sorbitol fatty acid esters such as POE(6) sorbitol monolaurate, POE(6) sorbitol hexastearate, POE(60) sorbitol tetrastearate, POE(6) sorbitol tetraoleate, POE(30) sorbitol tetraoleate, POE(40) sorbitol tetraoleate, and POE (60) sorbitol tetraoleate; condensation product of polyoxyethylene alkylphenyl formaldehyde such as condensation product of POE nonylphenyl formaldehyde; polyoxyethylene castor oils such as POE(3) castor oil, POE(10) castor oil, POE(20) castor oil, POE(40) castor oil, POE(50) castor oil, and POE(60) castor oil; polyoxyethylene hardened castor oils such as POE(5) hardened castor oil, POE(10) hardened castor oil, POE(20) hardened castor oil, POE(30) hardened castor oil, POE(40) hardened castor oil, POE(50) hardened castor oil, POE(60) hardened castor oil, POE(80) hardened castor oil, and POE(100) hardened castor oil; polyoxyethylene sterols such as POE(5) phytosterol, POE(10) phytosterol, POE(20) phytosterol, and POE(30) phytosterol; polyoxyethylene hydrogenated sterols such as POE(25) phytostanol and POE(30) cholestanol; polyethylene glycol fatty acid esters such as polyethylene glycol (10EO) monolaurate, polyethylene glycol (1EO) monostearate, polyethylene glycol (2EO) monostearate, polyethylene glycol (4EO) monostearate, polyethylene glycol (10EO) monostearate, polyethylene glycol (25EO) monostearate, polyethylene glycol (40EO) monostearate, polyethylene glycol (45EO) monostearate, polyethylene glycol (55EO) monostearate, polyethylene glycol (2EO) monooleate, polyethylene glycol (6EO) monooleate, polyethylene glycol (10EO) monooleate, ethylene glycol monostearate, ethylene glycol distearate, diethylene glycol stearate, polyethylene glycol distearate, and polyethylene glycol diisostearate; polyoxyethylene alkyl ethers such as POE(2) lauryl ether, POE(4. 2) lauryl ether, POE(9) lauryl ether, POE(21) lauryl ether, POE(25) lauryl ether, POE(2) cetyl ether, POE(5. 5) cetyl ether, POE(7) cetyl ether, POE(10) cetyl ether, POE(15) cetyl ether, POE(20) cetyl ether, POE(23) cetyl ether, POE(25) cetyl ether, POE(30) cetyl ether, POE(40) cetyl ether, POE (2) stearyl ether, POE(4) stearyl ether, POE(20) stearyl ether, POE(2) oleyl ether, POE(7) oleyl ether, POE(10) oleyl ether, POE(15) oleyl ether, POE(20) oleyl ether, POE(50) oleyl ether, POE(5) behenil ether, POE(10) behenil ether, POE (20) behenil ether, POE(30) behenil ether, POE(2) synthetic alkyl ether, POE(4) synthetic alkyl ether, POE(10) synthetic alkyl ether, POE(3) secondary alkyl ether, POE(5) secondary alkyl ether, POE(7) secondary alkyl ether, POE(9) secondary alkyl ether, and POE(12) secondary alkyl ether; polyoxyethylene polyoxypropylene alkyl ethers such as POE(1)POP(4) cetyl ether, POE(10)POP(4) cetyl ether, POE (20)POP(4) cetyl ether, POE(1)POP(8) cetyl ether, POE(20) POP(8) cetyl ether, POE(12)POP(6) decyl tetradecyl ether, POE(20)POP(6) decyl tetradecyl ether, POE(30)POP(6) decyl tetradecyl ether, acetic acid POE(3)POP(1) cetyl ether, and acetic acid POE(3)POP(1) isocetyl ether; polyoxyethylene alkylphenyl ethers such as POE(2) nonylphenyl ether, POE(5) nonylphenyl ether, POE(7. 5) nonylphenyl ether, POE(10) nonylphenyl ether, POE(15) nonylphenyl ether, POE(18) nonylphenyl ether, POE(20) nonylphenyl ether, POE(3) octylphenyl ether, and POE(10) octylphenyl ether, POE(30) octylphenyl ether; polyoxyethylene lanolin alcohols such as POE lanolin, POE(5) lanolin alcohol, POE(10) lanolin alcohol, POE(20) lanolin alcohol, and POE(40) lanolin alcohol; polyoxyethylene beeswax derivatives such as POE(6) sorbitol beeswax and POE(20) sorbitol beeswax; polyoxyethylene alkyl amines such as POE(5) stearyl amine, POE(10) stearyl amine, POE(15) stearyl amine, POE(5) oleyl amine, POE(15) oleyl amine, and POE(8) stearyl propylene diamine; and polyoxyethylene fatty acid amides such as POE(4) stearic acid amide, POE(15) stearic acid amide, and POE(15) oleic acid amide. In the above examples of the nonionic surface active agent having the hydroxyl group, the nonionic surface active agent which includes a polyoxyethylene chain is preferably employed. In the above examples, the terms "POE" and "POP" represent polyoxylethylene and polyoxypropylene, respectively.

The polymeric nonionic surface active agent is contained in the polymeric composition, generally in an amount of not smaller than 5% by weight, preferably in a range of 20–99.9% by weight, more preferably in a range of 50–99.5% by weight. When the amount of the nonionic surface active agent is smaller than 5% by weight, the obtained cleaning material does not exhibit a satisfactory cleaning effect.

The cross-linking agent as one of the essential constituents of the polymeric composition is copolymerized with the polymeric nonionic surface active agent as described above, or other ethylenically unsaturated monomers which will be described, so as to introduce a bridged structure in the contact lens cleaning material to be obtained. The contact lens cleaning material in which the bridged structure is formed is insoluble in water and exhibits not only improved mechanical properties, but also improved stability in configuration and improved durability. As the cross-linking agent to be used in the present invention, conventionally known cross-linking agents are suitably employed provided that they have a plurality of (at least two) polymerizable unsaturated double bonds such as (metha)acryloyl group, vinyl group, allyl group and vinylphenyl group.

Examples of the cross-linking agent are: ethylene glycol di(metha)acrylate, diethylene glycol di(metha)acrylate, triethylene glycol di(metha)acrylate, propylene glycol di(metha)acrylate, dipropylene glycol di(metha)acrylate, allyl(metha)acrylate, vinyl(metha)acrylate, trimethylol propane tri(metha)acrylate, methacryloyl oxyethyl acrylate, divinyl benzene, diallyl phthalate, diallyl adipate, triallyl isocyanurate, α-methylene-N-vinylpyrolidone, 4-vinylbenzyl(metha)acrylate, 3-vinylbenzyl(metha) acrylate, 2,2-bis[p-(metha)acryloyloxyphenyl] hexafluoropropane, 2,2-bis[m-(metha)acryloylosyphenyl] hexafluoropropane, 2,2-bis[o-(metha)acryloyloxyphenyl] hexafluoropropane, 2,2-bis[p-(metha)acryloyloxyphenyl] propane, 2,2-bis[m-(metha)acryloyloxyphenyl]propane, 2,2-bis[o-(metha)acryloyloxyphenyl]propane, 1,4-bis[2-(metha)acryloyloxyhexafluoroisopropyl]benzene, 1,3-bis[2-(metha)acryloyloxyhexafluoroisopropyl]benzene, 1,2-bis[2-(metha)acryloyloxyhexafluoroisopropyl]benzene, 1,4-bis[2-(metha)acryloyloxyisopropyl]benzene, 1,3-bis[2-(metha) acryloyloxyisopropyl]benzene, and 1,2-bis[2-(metha) acryloylosyisopropyl]benzene. It is preferable to employ the cross-linking agent which includes a unit of polyoxyethylene chain in each molecule.

The amount of the cross-linking agent contained in the polymeric composition is generally in a range of 0.01–5% by weight, preferably in a range of 0.1–3% by weight. If the amount of the cross-linking agent is below 0.01% by weight, the effect to be exhibited by the cross-linking agent is not sufficient. On the other hand, if the amount of the cross-linking agent exceeds the upper limit of 5% by weight, the obtained contact lens cleaning material tends to be fragile and is not suitable for practical use.

The polymeric composition may further contain, in addition to the above-described essential constituents, i.e., polymeric nonionic surface active agents and cross-linking agents, and other ethylenically unsaturated monomers that can be copolymerized with the essential constituents, as long as the addition of such monomers does not adversely influence the advantages of the present invention.

For instance, the polymeric composition may contain a disinfectant or germicide having a polymerizable unsaturated double bond such as (metha)acryloyl group, vinyl group or vinylphenyl group (hereinafter referred to as "polymeric germicide"), so that the obtained contact lens cleaning material exhibits a sterilizing effect. Any known polymeric germicides may be employed as long as they can be copolymerized with the above-described essential constituents of the polymeric composition. It is particularly preferable to employ a quaternary ammonium salt having a polymerizable unsaturated double bond (hereinafter referred to as "polymeric quaternary ammonium salt"). The polymeric quaternary ammonium salt is formed by reacting a quaternary ammonium salt having a hydroxyl group with an acid chloride having a polymerizable unsaturated double bond, or by reacting an amino compound having a polymerizable unsaturated double bond with an alkyl chloride. As one example of the method of forming the polymeric quaternary ammonium salt by the reaction of the amino compound having the polymerizable unsaturated double bond and the alkyl chloride, dimethyl aminoethyl(metha)acrylate is reacted with the alkyl chloride as indicated by the following formula (1), (1)

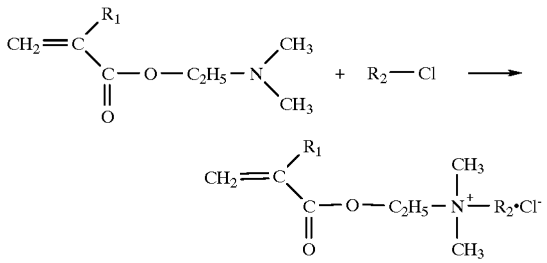

wherein, $R_1$ represents a hydrogen atom or a methyl group, and $R_2$ represents a hydrocarbon group having 1–30, preferably 8–30 carbon atoms.

Examples of the quaternary ammonium salt having the hydroxyl group (i.e., germicide) are quaternary ammonium salts indicated by the following formulas (2-1), (2-2) and (2-3).

(2–1)

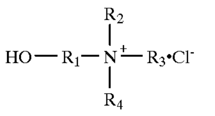

(2–2)

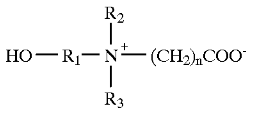

(2–3)

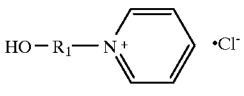

wherein $R_1$ represents a hydrocarbon group having 3–30, preferably 8–18 carbon atoms, $R_2$, $R_3$ and $R_4$ represent a same one or respective different ones of a hydrocarbon group having 1–30, preferably 1–8 carbon atoms and a benzyl group, and n represents one of integers “1” through “6”, preferably “1” through “3”.

The quaternary ammonium salt having the hydroxyl group is obtained by reaction of a trialkylamine compound and an alkylchloride hydroxide compound as indicated by the following formula (3), for instance.

(3)

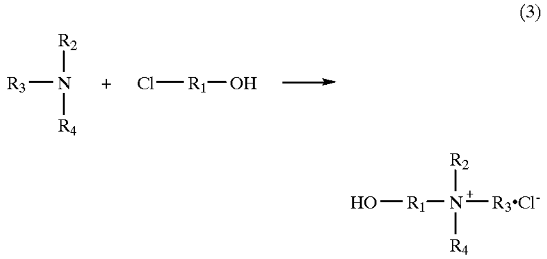

wherein $R_1$, $R_2$, $R_3$ and $R_4$ are the same as specified with respect to the above formulas (2-1) through (2-3).

The polymeric germicide is contained in the polymeric composition, generally in an amount of 0.01–10% by weight, preferably in an amount of 0.01–1% by weight. If the amount of the polymeric germicide is smaller than the lower limit of 0.01% by weight, the effect to be exhibited by the polymeric germicide is not sufficient. The sterilizing effect does not significantly increase with an increase in the amount of the polymeric germicide above the upper limit of 10% by weight. On the contrary, the amount of the polymeric germicide exceeding the upper limit may even deteriorate the strength of the contact lens cleaning material.

The polymeric composition of the present invention may further contain, as one of the other unsaturated monomers, a hydrophilic monomer which can be copolymerized with the above-described nonionic surface active agent and cross-linking agent (hereinafter referred to as “hydrophilic monomer”), so that the obtained contact lens cleaning material has a high degree of retention of the aqueous content. Examples of the hydrophilic monomer are: hydroxyalkyl (metha)acrylates such as hydroxyethyl(metha)acrylate, hydroxypropyl(metha)acrylate, hydroxybutyl(metha)acrylate, dihydroxypropyl(metha)acrylate and dihydroxybutyl(metha)acrylate; aminoalkyl(metha)acrylates such as aminoethyl(metha)acrylate, N-methylaminoethyl(metha)acrylate, N,N-dimethylaminoethyl(metha)acrylate, 2-dimethylaminoethyl (metha)acrylate, and 2-butylaminoethyl(metha)acrylate; (metha)acrylamides such as (metha)acrylamide, N-methyl (metha)acrylamide, N-ethyl(metha)acrylamide, N-hydroxyethyl(metha)acrylamide, N,N-dimethyl(metha)acrylamide, N,N-diethyl(metha)acrylamide, and N-ethyl-N-aminoethyl(metha)acrylamide; polyglycolmono(metha)acrylates such as diethyleneglycolmono(metha)acrylate, triethyleneglycolmono(metha)acrylate, and dipropyleneglycolmono(metha)acrylate; lactams such as N-vinylpyrrolidone, α-methylene-N-methylpyrrolidone, N-vinylcaprolactam, and N-(metha)acryloylpyrrolidone; (metha)acrylic acid; maleic anhydride; fumaric acid or its derivative; hydrophilic styrene derivatives such as dimethylaminostyrene and hydroxystyrene; morpholinoalkyl(metha)acrylates such as morpholinomethyl(metha)acrylate, and morpholinoethyl(metha)acrylate; methoxydiethyleneglycol (metha)acrylate; tetrahydrofurfuryl(metha)acrylate; 4-vinylpyridine; heterocyclic N-vinyl monomer such as vinyl imidazol, N-vinylpiperidone, N-vinylpyperidine, and N-vinylsuccinimide; N-(metha)acryloylpiperidine and N-(metha)acryloylmorpholine.

The polymeric composition may include a hydrophobic monomer as long as the addition of the hydrophobic monomer does not adversely influence the effect to be exhibited by the present contact lens cleaning material. Examples of the hydrophobic monomer are: linear, branched and cyclic alkyl(metha)acrylates such as methyl(metha)acrylate, ethyl (metha)acrylate, propyl(metha)acrylate, isopropyl(metha)acrylate, butyl(metha)acrylate, tert-butyl(metha)acrylate, isobutyl(metha)acrylate, pentyl(metha)acrylate, tert-pentyl (metha)acrylate, hexyl(metha)acrylate, heptyl(metha)acrylate, octyl(metha)acrylate, 2-ethylhexyl(metha)acrylate, nonyl(metha)acrylate, decyl(metha)acrylate, dodecyl (metha)acrylate, stearyl(metha)acrylate, cyclopentyl(metha)acrylate, and cyclohexyl(metha)acrylate; benzyl(metha)acrylate and isobornyl(metha)acrylate; hydrophobic styrene derivatives such as styrene, pentafluorostyrene, methylstyrene, trimethylstyrene, and trifluoromethylstyrene; fluorine-containing (metha)acrylates such as 2,2,2-trifluoroethyl(metha)acrylate, 1,1,1-trifluoro-2,2,2-trifluoroethyl(metha)acrylate, trifluoroethyl(metha)acrylate, tetrafluoropropyl(metha)acrylate, pentafluoropropyl(metha) acrylate, hexafluoroisopropyl(metha)acrylate, tetrafluoro-tert-pentyl(metha)acrylate, hexafluorobutyl(metha)acrylate, hexafluoro-tert-hexyl(metha)acrylate, ocafluoropentyl (metha)acrylate, 2,3,4,5,5,5-hexafluoro-2,4-bis (trifluoromethyl)pentyl(metha)acrylate, dodecafluoroheptyl (metha)acrylate, 2-hydroxyoctafluoro-6-trifluoromethylheptyl(metha)acrylate, 2-hydroxydodecafluoro-8-trifluoromethylnonyl(metha) acrylate, and 2-hydroxyhexadecafluoro-10-trifluoromethylundecyl(metha)acrylate; silicon-containing (metha)acrylates such as pentamethyldisiloxanylmethyl (metha)acrylate, pentamethyldisiloxanylpropyl(metha) acrylate, methylbis(trimethylsiloxy)silylpropyl(metha) acrylate, tris(trimethylsiloxy)silylpropyl(metha)acrylate, mono(methylbis(trimethylsiloxy)siloxy)bis (trimethylsiloxy) silylpropyl(metha)acrylate, tris(methylbis (trimethylsiloxy)siloxy)silylpropyl(metha)acrylate, methylbis(trimethylsiloxy)silylpropylglyceryl(metha) acrylate, tris(trimethylsiloxy)silylpropylglyceryl(metha) acrylate, mono(methylbis(trimethylsiloxy)siloxy)bis (trimethylsiloxy)silylpropylglyceryl(metha)acrylate, trimethylsilylethyltetramethyldisiloxanylpropylglyceryl (metha)acrylate, trimethylsilylmethyl(metha)acrylate, trimethylsilylpropyl(metha)acrylate, trimethylsilylpropylglyceryl(metha)acrylate, pentamethyldisiloxanylpropylglyceryl(metha)acrylate, methylbis(trimethylsiloxy) silylethyltetramethyldisiloxanylmethyl(metha)acrylate, tetramethyltriisopropylcyclotetrasiloxanylpropyl(metha) acrylate, and tetramethyltriisopropylcyclotetrasiloxybis (trimethylsiloxy)silylpropyl(metha)acrylate; silicon-containing styrene derivatives such as tris(trimethylsiloxy) silylstyrene, (pentamethyl-3,3-bis(trimethylsiloxy) trisiloxanyl)styrene, and (hexamethyl-3-trimethylsiloxytrisiloxanyl)styrene; alkoxy group-containing (metha)acrylates such as methoxyethyl(metha) acrylate and ethoxyethyl(metha)acrylate; aromatic ring-containing (metha)acrylates such as benzyl(metha)acrylate; alkylesters of unsaturated carboxylic acid such as itaconic acid, crotonic acid, maleic acid and fumaric acid which may be substituted by an alkyl group, a silicon-containing alkyl group and a siloxanyl alkyl group; and glycidyl(metha) acrylate.

For obtaining the contact lens cleaning material according to the present invention, the polymeric composition which is composed of various monomers as described above is copolymerized according to a known method such as radical polymerization.

For increasing compatibility and polymerization degree of the above-described various monomers which constitute the polymeric composition, the polymeric composition is preferably subjected to solution polymerization by using a suitable solvent. In the solution polymerization, a water-soluble solvent is preferably used. It is particularly preferable to employ a polar solvent whose boiling point is in a range of about 70–100° C. and which is capable of dissolving the polymeric composition. Examples of such a solvent are tetrahydrofuran (THF), propanol, ethanol and acetonitrile. Though the amount of the solvent to be used in the solution polymerization is not particularly limited, the solvent is preferably used in an amount more than twice that of the polymeric composition, when the polymeric surface active agent having a long alkyl chain in each molecule, because such a polymeric surface active agent is less likely to be dissolved with other monomers of the polymeric composition.

In polymerization of the polymeric composition, a filler such as a non-woven fabric may be included so as to improve the strength of the contact lens cleaning material to be obtained. The filler is included in the contact lens cleaning material by polymerizing the polymeric composition after the polymeric composition permeates into the filler, or after the filler is impregnated with the polymeric composition.

It is preferable that the present contact lens cleaning material contain a suitable aqueous component. The contact lens cleaning material containing the aqueous component is capable of absorbing the stains removed from the contact lens owing to the aqueous component functioning as a medium. Further, the contact lens cleaning material exhibits flexibility in the presence of the aqueous component, so as to facilitate the cleaning of the contact lens and eliminate a risk of damaging or scratching the contact lens during the cleaning.

The aqueous component included in the present contact lens cleaning material is not particularly limited. For instance, a physiological salt solution or an auxiliary tear fluid (artificial tear fluid) is used.

It is preferable that the present contact lens cleaning material have a content of the aqueous component generally in a range of 10–90%. If the content of the aqueous component is lower than 10%, the flexibility of the contact lens cleaning material tends to be insufficient, making it difficult to clean the contact lens. Further, the cleaning material is not likely to absorb the stains removed from the contact lens. If the content of the aqueous component exceeds 90%, the contact lens cleaning material does not exhibit a high degree of strength. In this case, the cleaning material tends to be broken during cleaning of the contact lens, and may not be used.

The present contact lens cleaning material may contain additional components other than the aqueous component as described above as long as those components do not adversely influence the effect to be exhibited by the present cleaning material. In case when the polymeric composition does not include the germicide, the obtained contact lens cleaning material may be impregnated with any known germicides which are usually used in the ophthalmologic field. Examples of such germicides are benzoic acid, sorbic acid and boric acid.

The contact lens cleaning material may be impregnated with a solution which is obtained by dissolving, in the aqueous component of the cleaning material, other additional components except the germicide as described just above. Examples of such additional components are a buffer agent, salt and thickener.

The buffer agent is used for adjusting a pH value of the aqueous component in the contact lens cleaning material. Any known buffer agents may be employed in the present contact lens cleaning material provided that they are ophthalmologically permissible, namely, they are allowed to be used with articles related to the contact lens. Examples of the buffer agent are sodium borate, sodium tetraborate, sodium methaborate, sodium citrate, citric acid, sodium hydrogencarbonate, tris(hydroxymethyl)aminomethane and phosphate buffer agent (e.g., $NaHPO_4$, $NaH_2PO_4$, $KH_2PO_4$). The amount of the buffer agent to be used in the contact lens cleaning material is generally in a range of 0.05–2.5% by weight, preferably in a range of 0.1–1.5% by weight.

The salt is used for adjusting tonicity of the aqueous component in the contact lens cleaning material. Any known salts may be employed in the present contact lens cleaning material provided that they are ophthalmologically permissible, namely, they are allowed to be used with the articles related to the contact lens. For instance, sodium chloride or potassium chloride is used. The amount of the salt to be used is not particularly limited, but may be suitably determined such that the tonicity of the aqueous component of the contact lens cleaning material is substantially equal to the osmotic pressure of the ordinary tear fluid.

The thickener is used for adjusting the viscosity of the aqueous component in the contact lens cleaning material, so as to facilitate the use of the cleaning material to be obtained. Any known thickeners may be employed as long as they are ophthalmologically permissible, namely, they are allowed to be used with the articles related to the contact lens. Examples of the thickener are: cellulose derivatives such as methylcellulose, carboxymethylcellulose, carboxyethylcellulose, hydroxyethylcellulose, and hydroxypropyldellulose; gums of hetero polysaccharides such as guar gum, locust bean gum, quince seed gum, tara gum, tragacanth gum, karaya gum, xanthan gum, welan gum, rhamsan gum, carageenan, and gum arabic; alginic acid derivatives such as sodium alginate, ammonium alginate, and propyleneglycolester alginate; starch derivatives such as sodium carboxymethyl starch and hydroxyethyl starch; dextrin pectin; gelatin; casein; synthetic organic high-molecular compounds such as polyvinyl alcohol, polyvinyl pyrrolidone, polyethylene oxide, polyacrylic acid, poly (sodium acrylate), and polyacryl amide; homopoylmers and copolymers such as N,N-dimethylaminoethyl(metha) acrylate, salts of 2-methacryloyloxyethyltrimethyl ammonium chloride, N,N-dimethyl-3-aminopropyl(metha) acrylate, salts of 3-methacryloyloxypropyltrimethyl ammonium chloride, N,N-dimethyl-3-amino-(3-methylbutyl) (metha)acrylate, salts of 3-methacryloyloxy-(3-methylbutyl)trimethyl ammonium chloride, salts of 3-methacryloyloxy-(2-hydroxypropyl)-N,N,N-trimethyl ammonium chloride, salts of diallyldimethyl ammonium chloride, salts of vinylbenzyltrimethyl ammonium chloride, 2-vinylpyridine, 4-vinylpyridine, 2-methyl-5-vinylpyridine, salts of 2-methyl-5-vinylpyridiniumchloride, 1-vinyl imidazole, 2-methyl-1-vinyl imidazole, and salts of 1-vinyl imidazolium chloride, cationic starch, cationic cellulose, ionene polymer; salts of carboxymethylcellulose, salts of sodium carboxymethylhydroxyethylcellulose, salts of sodium carboxymethyl starch, salts of sodium carboxymethylhydroxyethyl starch; homopolymers and copolymers such as salts of sodium (metha)acrylate, salts of sodium vinylsulfonate, salts of sodium p-styrenesulfonate, salts of sodium 2-methacryloyloxyethylsulfonate, salts of sodium 3-methacryloyloxy-2-hydroxysulfonate, salts of sodium 2-acrylamide-2-methylpropanesulfonate, salts of sodium allylsulfonate, and salts of sodium 2-phosphateethylmethacrylate. The amount of the thickener to be used in the contact lens cleaning material is generally in a range of 0.01–10.0% by weight, preferably in a range of 0.01–3.0% by weight.

The present contact lens cleaning material is in a suitable solid form. The configuration of the cleaning material is not particularly limited, but may be suitably determined depending upon the application of the contact lens cleaning material. For example, the contact lens cleaning material may be in the form of a sheet, plate or sponge. For easy handling of the contact lens cleaning material, it is preferable that the contact lens cleaning material be in the form of a sheet. For obtaining such a sheet-type cleaning material, the polymeric composition is cast in a sheet form upon polymerization thereof, so that the cleaning material is formed into the sheet form concurrently when the polymeric composition is polymerized. Alternatively, the polymeric composition is formed into a polymer having a suitable shape such as a cylindrical shape. Then, the obtained polymer is sliced into a plurality of sheets.

When the sheet-type contact lens cleaning material is used for cleaning the contact lens, the cleaning material is folded so as to cover or wrap the contact lens. Then, the contact lens covered with the cleaning material is subjected to finger-rubbing. When the contact lens cleaning material is in the form of a sponge (e.g., cleaning puff), the contact lens is placed on the sponge-type cleaning material, and is cleaned by finger-rubbing.

The contact lens cleaning material according to the present invention may be throw-away type. Such a throw-away type cleaning material assures further improved handling and portability thereof.

The contact lens cleaning material according to the present invention is wrapped in a simplified manner with suitable means such as a retorted package. If the sterilizing treatment is effected on the wrapped cleaning material, the cleaning material assures a high degree of safety without containing the germicide therein.

EXAMPLES

To further clarify the concept of the present invention, some examples of the invention will be described. It is to be understood that the invention is not limited to the details of the illustrated examples, but may be embodied with various changes, modifications and improvements, which may occur to those skilled in the art without departing from the scope of the invention defined in the attached claims.

Example 1

Initially, there was prepared a solution by dissolving, in 20 mL of tetrahydrofuran as a reaction solvent, 6.0 g of acryloylpolyoxyethylene(40) cetylether as a polymeric nonionic surface active agent, 2.0 g of polyoxyethylene(14) diacrylate as a cross-linking agent, 1.0 g of acryloylcetyltriethyl ammonium chloride as a germicide, and 0.1 g of azobisisobutyronitrile as a polymerization initiator. A nonwoven fabric (as a filler) having a size of 100 $cm^2$ was impregnated with the obtained solution, and put into a container which had been subjected to deoxidation treatment. Then, the container was subjected to thermal polymerization at 50° C. for 8 hours, so as to provide a film-like contact lens cleaning material reinforced by the non-woven fabric, according to the present invention. After the obtained film-like cleaning material was washed under the flowing water for one hour, it was cut into pieces each of which has a rectangular shape having a width of 3 cm and a length of 5 cm. Then, the cleaning material was boiled in 500 mL of physiological salt solution for 8 hours so as to remove unpolymerized monomers and the solvent. Thereafter, the cleaning material was stored in physiological salt solution.

Next, an eluting material test was effected on the film-like cleaning material obtained as described above in the following manner. Initially, there was prepared a 200 mL-Erlenmeyer flask having a lid filled with 150 mL of distilled water. 3.00 g of the accurately measured film-like cleaning material which had been air-dried at room temperature was put into the Erlenmeyer flask. As a control, there was prepared another 200 mL-Erlenmeyer flask having a lid in which only 150 mL of distilled water was poured. The two flasks were subjected to thermal reflux at 100° C. for 30 minutes. Subsequently, the two flasks were cooled down to room temperature, so as to provide a specimen solution and a control solution, respectively. To 10 mL of the respective two solutions, there were added 50 mL of 0.01N solution of potassium permanganate and 1.0 mL of 10% dilute sulfuric acid by using a volumetric pipet. After the solutions were boiled for three minutes, they were cooled down to room temperature. To the respective two solutions, potassium iodide in an amount of 0.1±0.05 g measured in the unit of 1 mg and five droplets of starch solution were added and mixed well. The obtained two solutions were respectively titrated by using 0.01N sodium thiosulfate. The amount of the solution of potassium permanganate consumed by the material eluted from the contact lens cleaning material was calculated according to the following equation (1). The amount of consumption of the 0.01N solution of potassium permanganate was lower than 2.0 mL.

| |
|---|
| the amount of the potassium permanganate solution consumed by the eluting material (mL) = (B − S) × T . . . (1) |

wherein

B: the amount (mL) of the sodium thiosulfate solution required for titrating the control solution, S: the amount (mL) of the sodium thiosulfate solution required for titrating the specimen solution, and T: the potency of 0.01N sodium thiosulfate Example 2

The film-like contact lens cleaning material reinforded by the non-woven fabric according to the present invention was obtained as in the above Example 1, by dissolving, in 20 mL of tetrahydrofuran as the reaction solvent, 6.0 g of acryloylpolyoxyethylene(20) nonylphenylether as the polymeric nonionic surface active agent, 2.0 g of polyoxyethylene(9) diacrylate as the cross-linking agent, and 0.1 g of azobisisobutyronitrile as the polymerization initiator. The obtained film-like cleaning material was put into a retort container. After the container was sealed, it was heated for the sterilizing treatment. The amount of the potassium permanganate solution consumed by the eluting material was calculated as in the above Example 1. The amount of consumption of the 0.01N solution of potassium permanganate was lower than 2.0 mL.

Example 3

The film-like contact lens cleaning material reinforced by the non-woven fabric according to the present invention was obtained as in the above Example 1, by dissolving, in 20 mL of tetrahydrofuran as the reaction solvent, 2.0 g of acryloylpolyoxyethylene(20) secondary alkylether and 4.0 g of acryloylpolyoxyethylene(20) cetylether as the polymeric nonionic surface active agent, 1.0 g of polyoxyethylene(9) diacrylate as the cross-linking agent, 1.0 g of acryloyloxycetyl pyridinium bromide as the germicide, and 0.1 g of azobisisobutyronitrile as the polymerization initiator. The amount of the potassium permanganate solution consumed by the eluting material was calculated as in the above Example 1. The amount of consumption of the 0.01N solution of potassium permanganate was lower than 2.0 mL.

Example 4

The film-like contact lens cleaning material reinforced by the non-woven fabric according to the present invention was obtained as in the above Example 1, by dissolving, in 20 mL of distilled water as the reaction solvent, 6.0 g of acryloylpolyoxyethylene(30) cetylether as the polymeric nonionic surface active agent, 2.0 g of polyoxyethylene(9) diacrylate as the cross-linking agent, 1.0 g of dodecyldimethylethylacrylate ammonium bromide as the germicide, 0.5 g of hydroxyethyl acrylate as the hydrophilic monomer, and 0.1 g of potassium persulfate as the polymerization initiator. The amount of the potassium permanganate solution consumed by the eluting material was calculated as in the above Example 1. The amount of consumption of the 0.01N solution of potassium permanganate was lower than 2.0 mL.

Example 5

In 100 mL of tetrahydrofuran as the reaction solvent, there were dissolved 20.0 g of acryloylpolyoxyethylene(40) dodecylether as the polymeric nonionic surface active agent, 10.0 g of polyoxyethylene(14) diacrylate as the cross-linking agent, 5.0 g of acryloyloxycetylpyridiniumbromide as the germicide, 2.0 g of hydroxyethylacrylate as the hydrophilic polymeric component, and 0.5 g of azobisisobutyronitrile as the polymerization initiator. In a tube-like polymerization container (having a diameter of 50 mmϕ and a length of 100 mm), absorbent cotton was packed. The absorbent cotton was impregnated with the solution prepared as described above, and subjected to deoxidation treatment. Then, the container in which the absorbent cotton impregnated with the solution was packed was heated at 50° C. for 8 hours for thermal polymerization. The thus obtained polymer was soaked in a large amount of distilled water for 3 days so as to substitute with the distilled water, for the purpose of removing the unpolymerized monomers and the solvent from the obtained polymer. Thereafter, the polymer which is impregnated with water was cut into pieces each having a thickness of 1 mm, so as to provide the film-like contact lens cleaning material according to the present invention. After the obtained cleaning material was boiled in 500 mL of physiological salt solution for 8 hours, it was stored in physiological salt solution. The amount of the potassium permanganate solution consumed by the eluting material was calculated as in the above Example 1. The amount of consumption of the 0.01N solution of potassium permanganate was lower than 2.0 mL.

Example 6

The film-like contact lens cleaning material reinforced by the absorbent cotton according to the present invention was obtained as in the above Example 5, by dissolving, in 100 mL of distilled water as the reaction solvent, 20.0 g of acryloylpolyoxyethylene(40) cetylether as the polymeric nonionic surface active agent, 10.0 g of polyoxyethylene(14) diacrylate as the cross-linking agent, 5.0 g of N-dodecyl-N, N-dimethyl-N-(methacryloyloxyethyl) ammonium bromide as the germicide, 2.0 g of hydroxyethylacrylate as the hydrophilic polymeric component, and 0.5 g of potassium persulfate as the polymerization initiator. The amount of the potassium permanganate solution consumed by the eluting material was calculated as in the above Example 1. The amount of consumption of the 0.01N solution of potassium permanganate was lower than 2.0 mL.

Example 7

In 15 mL of propanol as the reaction solvent, there were dissolved 6.0 g of acryloylpolyoxyethylene(40) cetylether as the polymeric nonionic surface active agent, 2.0 g of polyoxyethylene(14) diacrylate as the cross-linking agent, 1.0 g of acryloylcetyltriethyl ammonium chloride as the polymeric germicide, and 0.5 g of "Darocure 1173"

(available from Merck & Co., Inc., U.S.A., namely, phenyl-2-hydroxy-2-propylketone). After the non-woven fabric (filler) having a size of 100 $cm^2$ was impregnated with the thus obtained solution, it was put into a container which had been subjected to deoxidation treatment. Then, the ultraviolet rays were irradiated on the container at 30° C. for 30 minutes. The container was subjected to heat-treatment at 70° C. for 3 hours, for the purpose of vaporizing the solvent and completing the polymerization, so as to provide the film-like contact lens cleaning material reinforced by the non-woven fabric according to the present invention. After the obtained film-like contact lens cleaning material was washed under the flowing water for one hour, it was cut into pieces each of which has a rectangular shape having a width of 3 cm and a length of 5 cm. Then, the cleaning material was boiled in 500 mL of physiological salt solution for 8 hours, and the unpolymerized monomers and the solvent were removed therefrom. Subsequently, the cleaning material was stored in physiological salt solution. The amount of the potassium permanganate solution consumed by the eluting material was calculated as in the above Example 1. The amount of consumption of the 0.01N solution of potassium permanganate was lower than 2.0 mL.

Example 8

The film-like contact lens cleaning material reinforced by the non-woven fabric according to the present invention was obtained as in the above Example 7, by dissolving, in 15 mL of n-hexanol as the reaction solvent, 6.0 g of acryloylpolyoxyethylene(20) nonylphenylether as the polymeric nonionic surface active agent, 2.0 g of polyoxyethylene(9) diacrylate as the cross-linking agent, and 0.5 g of Darocure 1173 as the photopolymerization initiator. The obtained film-like cleaning material was put into the retort container. After the container was sealed, it was heated for the sterilizing treatment. The amount of the potassium permanganate solution consumed by the eluting material was calculated as in the above Example 1. The amount of consumption of the 0.01N solution of potassium permanganate was lower than 2.0 mL.

Example 9

The film-like contact lens cleaning material reinforced by the non-woven fabric according to the present invention was obtained as in the above Example 7, by dissolving, in 15 mL of n-hexanol as the reaction solvent, 2.0 g of acryloylpolyoxyethylene(20) secondary alkylether and 4.0 g of acryloylpolyoxyethylene(20) cetylether as the polymeric nonionic surface active agent, 1.0 g of polyoxyethylene(9) diacrylate as the cross-linking agent, 1.0 g of acryloyloxycetylpyridiniumbromide as the polymeric germicide, and 0.5 g of Darocure 1173 as the photopolymerization initiator. The amount of the potassium permanganate solution consumed by the eluting material was calculated as in the above Example 1. The amount of consumption of the 0.01N solution of potassium permanganate was lower than 2.0 mL.

Example 10

In 15 mL of propanol as the reaction solvent, there were dissolved 5 g of polyoxyethylene-poloxypropyrene block polymer whose ends are methacrylated (hereinafter referred to as "Plonon 204 dimethacrylate") as the polymeric nonionic surface active agent, 25 g of dimethylacrylamide (hereinafter referred to as "DMAA") as the hydrophilic monomer, 70 g of laurylmethacrylate (hereinafter referred to as "LMA") as the hydrophobic monomer, 0.1 g of ethyleneglycol dimethacrylate (hereinafter referred to as "EDMA") as the cross-linking agent, 0.5 g of trimethylethylmethacrylate ammonium chloride (hereinafter referred to as "TEMAC") as the polymeric germicide, and 0.1 g of 2,2'-azobis(2,4-dimethylvaleronitrile) (hereinafter referred to as "V-65") as the polymerization initiator.

The thus obtained solution was accommodated in an enclosed space (whose width, length and thickness are 5 cm, 10 cm and 5 mm, respectively), and was heated at 50° C. for 8 hours for thermal polymerization, so as to provide the film-like contact lens cleaning material according to the present invention. The enclosed space was defined by two sheets of glass and a frame formed of a fluoroethylene resin, such that the frame is interposed between the two sheets of glass. After the obtained film-like cleaning material was washed under the flowing water for one hour, it was cut into pieces each of which has a rectangular shape having a width of 3 cm and a length of 5 cm. The cleaning material was then boiled in 500 mL of physiological salt solution for 8 hours so as to remove unpolymerized monomers and the solvent therefrom. Thereafter, the cleaning material was stored in physiological salt solution. The amount of the potassium permanganate solution consumed by the eluting material was calculated as in the above Example 1. The amount of consumption of the 0.01N solution of potassium permanganate was lower than 2.0 mL.

Example 11

The film-like contact lens cleaning material according to the present invention was obtained as in the above Example 10, by dissolving, in 15 mL of propanol as the reaction solvent, 5 g of methacryloylpolyoxyethylene(20) laurylether as the polymeric nonionic surface active agent, 25 g of DMAA as the hydrophilic monomer, 70 g of LMA as the hydrophobic monomer, 0.1 g of EDMA as the cross-linking agent, 0.5 g of TEMAC as the polymeric germicide, and 0.1 g of V-65 as the polymerization initiator. The amount of the potassium permanganate solution consumed by the eluting material was calculated as in the above Example 1. The amount of consumption of the 0.01N solution of potassium permanganate was lower than 2.0 mL.

Example 12

In 15 mL of propanol as the reaction solvent, there were dissolved 10 g of Plonon 204 dimethacrylate as the polymeric nonionic surface active agent, 15 g of DMAA and 15 g of N-vinylpyrrolidone (hereinafter referred to as "N-VP") as the hydrophilic monomer, 60 g of 2-ethylhexylmethacrylate as the hydrophobic monomer, 0.1 g of EDMA as the cross-linking agent, 0.5 g of TEMAC as the polymeric germicide, and 0.1 g of Darocure 1173 as the photopolymerization initiator.

Subsequently, the obtained solution was accommodated in the enclosed space (having a thickness of 5 mm) defined by and between the two sheets of glass, as in the above Example 10. The solution in the enclosed space was polymerized by irradiation of the ultraviolet rays at 30° C. for 30 minutes. The solution was then heat-treated at 70° C. for 3 hours, for the purpose of vaporizing the solvent and completing the polymerization, so as to provide the film-like contact lens cleaning material. After the obtained film-like cleaning material was washed under the flowing water for one hour, it was cut into pieces each of which has a rectangular shape having a width of 3 cm and a length of 5 cm. The cleaning material was then boiled in 500 mL of physiological salt solution for 8 hours, for removal of the unpolymerized monomers and the solvent therefrom. Subsequently, the cleaning material was stored in physiological salt solution. The amount of the potassium permanganate solution consumed by the eluting material was calculated as in the above Example 1. The amount of the consumption of the 0.01N solution of potassium permanganate was lower than 2.0 mL.

Example 13

The film-like contact lens cleaning material according to the present invention was obtained as in the above Example 12, by dissolving, in 15 mL of propanol as the reaction product, 10 g of methacryloylpolyoxyethylene(6) octylphenylether as the polymeric nonionic surface active agent, 30 g of N-VP as the hydrophilic monomer, 60 g of LMA as the hydrophobic monomer, 0.1 g of EDMA as the cross-linking agent, 0.5 g of TEMAC as the polymeric germicide, and 0.1 g of Darocure 1173 as the photopolymerization initiator. The amount of the potassium permanganate solution consumed by the eluting material was calculated as in the above Example 1. The amount of consumption of the 0.01N solution of potassium permanganate was lower than 2.0 mL.

Example 14

The film-like contact lens cleaning material according to the present invention was obtained as in the above Example 12, by dissolving, in 15 mL of propanol as the reaction product, 10 g of Plonon 204 dimethacrylate as the polymeric nonionic surface active agent, 40 g of hydroxyethylmethacrylate as the hydrophilic monomer, 50 g of LMA as the hydrophobic monomer, 0.1 g of EDMA as the cross-linking agent, and 0.1 g of Darocure 1173 as the photopolymerization initiator. The obtained film-like contact lens cleaning material was put into the retort container. After the container was sealed, it was heated for the sterilizing treatment. The amount of the potassium permanganate solution consumed by the eluting material was calculated as in the above Example 1. The amount of consumption of the 0.01N solution of potassium permanganate was lower than 2.0 mL.

Example 15

The film-like contact lens cleaning material according to the present invention was obtained as in the above Example 12, by dissolving, in 15 mL of propanol as the reaction product, 5 g of Plonon 204 dimethacrylate as the polymeric nonionic surface active agent, 25 g of DMAA as the hydrophilic monomer, 70 g of LMA as the hydrophobic monomer, 0.1 g of EDMA as the cross-linking agent, and 0.1 g of Darocure 1173 as the photopolymerization initiator. The obtained film-like contact lens cleaning material was put into the retort container. After the container was sealed, it was heated for the sterilizing treatment. The amount of the potassium permanganate solution consumed by the eluting material was calculated as in the above Example 1. The amount of consumption of the 0.01N solution of potassium permanganate was lower than 2.0 mL.

Example 16

The film-like contact lens cleaning material reinforced by the non-woven fabric according to the present invention was obtained as in the above Example 1, by dissolving, in 15 mL of propanol as the reaction product, 5 g of Plonon 204 dimethacrylate as the polymeric nonionic surface active agent, 25 g of DMAA as the hydrophilic monomer, 70 g of LMA as the hydrophobic monomer, 0.1 g of EDMA as the cross-linking agent, 0.5 g of TEMAC as the polymeric germicide, and 0.1 g of V-65 as the polymerization initiator. The amount of the potassium permanganate solution consumed by the eluting material was calculated as in the above Example 1. The amount of consumption of the 0.01N solution of potassium permanganate was lower than 2.0 mL.

Example 17

The film-like contact lens cleaning material reinforced by the non-woven fabric according to the present invention was obtained as in the above Example 7, by dissolving, in 15 mL of propanol as the reaction product, 10 g of methacryloylpolyoxyethylene(6) octylphenylether as the polymeric nonionic surface active agent, 30 g of N-VP as the hydrophilic monomer, 60 g of LMA as the hydrophobic monomer, 0.1 g of EDMA as the cross-linking agent, 0.5 g of TEMAC as the polymeric germicide, and 0.1 g of Darocure 1173 as the photopolymerization initiator. The amount of the potassium permanganate solution consumed by the eluting material was calculated as in the above Example 1. The amount of consumption of the 0.01N solution of potassium permanganate was lower than 2.0 mL.

Example 18

The film-like contact lens cleaning material reinforced by the non-woven fabric according to the present invention was obtained as in the above Example 7, by dissolving, in 15 mL of propanol as the reaction product, 5 g of Plonon 204 dimethacrylate as the polymeric nonionic surface active agent, 25 g of DMAA as the hydrophilic monomer, 70 g of LMA as the hydrophobic monomer, 0.1 g of EDMA as the cross-linking agent, and 0.1 g of Darocure 1173 as the photopolymerization initiator. The obtained film-like cleaning material was put into the retort container. After the container was sealed, it was heated for the sterilizing treatment. The amount of the potassium permanganate solution consumed by the eluting material was calculated as in the above Example 1. The amount of consumption of the 0.01N solution of potassium permanganate was lower than 2.0 mL.

In all of the above Examples 1–18, the amount of the potassium permanganate solution consumed by the eluting material was lower than 2.0 mL. Thus, it was confirmed that substantially no eluting material was generated in the present contact lens cleaning material. In general, if the organic compound of the contact lens cleaning material is eluted therefrom, the potassium permanganate is consumed to oxidize the organic compound. In the above Examples 1–18, however, the potassium permanganate is not substantially consumed. Accordingly, it was confirmed that the components of the present contact lens cleaning material are less likely to be eluted therefrom.

Example 19

The contact lens cleaning material according to the present invention was examined of its cleaning effect with respect to the stains adhering to the contact lens. There were prepared two kinds of the contact lenses, i.e., “SUPER EX” and “SOFT S” both available from Menicon Co., Ltd., Japan. 180 contact lenses were prepared for each kind. After these contact lenses were worn for one day, they were cleaned by rubbing, using the present contact lens cleaning materials obtained in the above Examples 1–18 (i.e., 10 contact lenses for each of the cleaning materials obtained in the Examples 1–18). After, each of the contact lenses was rinsed by physiological salt solution, it was examined of its surface by a microscope. The result of the examination showed that the stains such as fats which had adhered to the contact lens before cleaning thereof were removed. Thus, it was confirmed that the contact lens cleaning material according to the present invention exhibits a high degree of detergency.

Example 20

The present contact lens cleaning material was examined of its effect on the contact lens while the contact lens is cleaned by using the cleaning material. There were prepared four kinds of contact lenses, i.e., "SUPER EX", "MENICON HARD", "MENICON SOFT S", and "SOFT MA" all available from Menicon Co., Ltd., Japan. 36 contact lenses were prepared for each kind. The contact lenses were cleaned by rubbing for 10 minutes, using the present contact lens cleaning materials obtained in the above Examples 1–18. (i.e., 2 contact lenses for each of the cleaning materials obtained in Examples 1–18). After each of the contact lenses was rinsed with physiological salt solution, it was examined by the microscope for any scratches on its surface. The result of the examination showed that the lens had no scratches and that the specification of the contact lens was not influenced after the contact lens was cleaned by the present cleaning material. Thus, it was confirmed that the contact lens cleaning material of the present invention neither gives any damage on the contact lens nor causes deformation of the contact lens.

It will be apparent from the above description that the present contact lens cleaning material is capable of cleaning the contact lens in a considerably simplified manner while exhibiting a sufficiently high degree of detergency and excellent portability. In particular, the present contact lens cleaning material can be suitably used to clean soft contact lenses and oxygen permeable contact lenses.

The present contact lens cleaning material contains the nonionic surface active agent which is bonded to the polymer that provides the cleaning material. Accordingly, the contact lens cleaning material exhibits a high degree of detergency for assuring excellent cleaning effect. Further, the present contact lens cleaning material is free from elution of the nonionic surface active agent therefrom.

When the contact lens cleaning material contains the germicide which is bonded to the polymer that provides the cleaning material, the contact lens cleaning material exhibits an excellent sterilizing effect without suffering from elution of the germicide therefrom, so that the present contact lens cleaning material is free from the possibility that the germicide eluted therefrom may permeate into the contact lens, and accordingly give an adverse influence on the eyes of the user. Further, the contact lens cleaning material containing the germicide bonded to the polymer thereof exhibits antimicrobial activity so as to assure excellent storage capability.

When the present contact lens cleaning material in the form of gel that contains the aqueous component, the cleaning material absorbs the stains which are removed from the contact lens. Thus, the present contact lens cleaning material effectively prevents the stains once removed from the contact lens from adhering back to the contact lens.

Since the contact lens cleaning material of the present invention is soft, and preferably contains the aqueous component, it is not likely to damage the material of the contact lens after the contact lens is cleaned by using the cleaning material.

The present contact lens cleaning material permits easy cleaning of the contact lens even where a conventionally cleaning agent or device is not available, and electric power source for driving the device is not available.

What is claimed is:

1. A contact lens cleaning material in a solid form, said material being formed of a polymer obtained by polymerizing a polymeric composition including: not less than 5 wt. % of a polyoxethylated nonionic surface active agent having an ethylenically unsaturated double bond, and 0.01 to 5 wt. % of a cross-linking agent having a plurality of ethylenically unsaturated double bonds.

2. A contact lens cleaning material according to claim 1, wherein said polymeric composition further includes 0.01 to 10 wt. % of a disinfectant having an ethylenically unsaturated double bond.

3. A contact lens cleaning material according to claim 2, wherein said disinfectant is included in said polymeric composition in an amount of 0.01–1% by weight.

4. A contact lens cleaning material according to claim 2, wherein said disinfectant is a quaternary ammonium salt having a polymerizable unsaturated double bond.

5. A contact lens cleaning material according to claim 1, wherein said nonionic surface active agent is included in said polymeric composition in an amount of 20–99.9% by weight.

6. A contact lens cleaning material according to claim 1, wherein said nonionic surface active agent is included in said polymeric composition in an amount of 50–99.9% by weight.

7. A contact lens cleaning material according to claim 1, wherein said cross-linking agent is included in said polymeric composition in an amount of 0.1–3% by weight.

8. A contact lens cleaning material according to claim 1, wherein said polymeric composition further includes a hydrophilic monomer having a polymerizable unsaturated double bond.

9. A contact lens cleaning material according to claim 1, wherein said polymeric composition is dissolved in a solvent and polymerized.

10. A contact lens cleaning material according to claim 1, having a content of an aqueous component in a range of 10–90%.

11. A contact lens cleaning material according to claim 1, further including a filler.

12. A contact lens cleaning material according to claim 1, wherein said polymer is in the form of a gel which contains an aqueous component.

13. A contact lens cleaning material according to claim 1, wherein said solid form is selected from the group consisting of a sheet, a plate and a sponge.

* * * * *